United States Patent [19]

Ko et al.

[11] Patent Number: 4,913,152

[45] Date of Patent: Apr. 3, 1990

[54] MAGNETOENCEPHALOGRAPH (MEG) USING A MULTI-AXIS MAGNETIC GRADIOMETER FOR LOCALIZATION AND TRACKING OF NEUROMAGNETIC SIGNALS

[75] Inventors: Harvey W. Ko, Columbia; Joseph P. Skura, Ellicott City; Harry A. C. Eaton, Columbia, all of Md.

[73] Assignee: The Johns Hopkins University, Baltimore, Md.

[21] Appl. No.: 390,495

[22] Filed: Aug. 1, 1989

Related U.S. Application Data

[63] Continuation of Ser. No. 187,620, Apr. 28, 1988, abandoned.

[51] Int. Cl.[4] .................................................. A61B 5/05
[52] U.S. Cl. .................................................. 128/653 R
[58] Field of Search ................ 128/653, 731; 324/244, 324/248, 253, 254, 258, 260

[56] References Cited

U.S. PATENT DOCUMENTS

| | | | |
|---|---|---|---|
| 4,700,135 | 10/1987 | Hoenig | 324/248 |
| 4,736,751 | 4/1988 | Gevins et al. | 128/731 |
| 4,753,246 | 6/1988 | Freeman | 128/731 |
| 4,793,355 | 12/1988 | Crum et al. | 128/653 |

OTHER PUBLICATIONS

Wynn et al., "Advanced Superconducting Gradiometer/Magnetometer Arrays and a Novel Signal Processing Technique", IEEE Transactions on Magnetics, vol. MAG-11, No. 2, Mar. 1975, pp. 701-707.

*Primary Examiner*—Ruth S. Smith
*Attorney, Agent, or Firm*—Robert E. Archibald; Howard W. Califano

[57] ABSTRACT

An apparatus and method for the passive, non-invasive magnetoencephalographic (MEG) localization and tracking of sources of magnetic signals in the brain is disclosed. The apparatus and method uses a multi-axis magnetic gradiometer to detect the magnetic field, field gradient, and polarization emanating from neuronal sources in the brain under either normal or pathological conditions.

7 Claims, 3 Drawing Sheets

SINGLE COIL
MAGNETOMETER

FIRST ORDER
GRADIOMETER

SECOND ORDER
GRADIOMETER

THIRD ORDER
GRADIOMETER

MAGNETOENCEPHALOGRAPH (MEG) USING A MULTI-AXIS MAGNETIC GRADIOMETER FOR LOCALIZATION AND TRACKING OF NEUROMAGNETIC SIGNALS

STATEMENT OF GOVERNMENTAL INTEREST

The Government has rights in this invention pursuant to Contract No. N00024-85-C-5301 awarded by the Department of the Navy.

This is a continuation of co-pending application Ser. No. 07/187,620 filed on Apr. 28, 1988, now abandoned.

BACKGROUND OF THE INVENTION

1. Field of the Invention

The invention relates to a method and apparatus for locating the neuronal sources of magnetic signals emanating from the brain under normal or pathological conditions. Neuromagnetic signals seen under normal conditions might result from evoked responses from visual, auditory, somatic, or other type stimulus. Normal signals may also be used to study a patient's brain rhythms, such as alpha, beta, etc. Neuromagnetic signals seen under pathological conditions might be associated with epilepsy or some other disease.

2. Description of the Contemporary and/or Prior Art

Locating neuronal sources of magnetic signals emanating from the brain under normal or pathological conditions is of significance in clinical diagnostics. Neuromagnetic signals seen under normal conditions might measure evoked responses from visual, auditory, somatic, or other type of stimulus. Normal signals might also be used to study brain rhythms, such as alpha and beta brain rhythms. Neuromagnetic signals seen under pathological conditions might be associated with epilepsy or some other disease.

The neuromagnetic signals that originate from sources in the brain can be modeled by current dipoles. The current dipole causes volume currents, J, to flow in the brain that, at the brain surface, cause potential differences, V, at the scalp, which are signals measured by the EEG (electroencephalograph). A magnetic field, B, associated with the current dipole is also generated and is the neuromagnetic field measured by the MEG (magnetoencephalograph). The neuromagnetic field has a field spatial pattern giving contours of constant field (plus contours for the B field vector coming out, minus contours for the B field vector going in). The magnitude of the field diminishes as the contour radius increases.

The MEG has theoretical advantages over the EEG. The vector B gives directional information about the source orientation. The neuromagnetic field B is not distorted by the brain, which has the same permeability as air. The MEG is an absolute measure of source strength not measured with respect to a reference, as is the EEG. The MEG is not affected by bad electrode contact or tissue artifacts, as is the EEG. The MEG does not need to touch the head, as in the EEG.

The prior art apparatus and method requires movement of the MEG to a plurality of positions over the skull of the patient. At each position data is collected. A contour map is then drawn from the data and the dipole location is found along a line drawn connecting the plus peak contour with the minus peak contour at a depth using algebraic theory for a dipole in a sphere. Several problems occur with this prior art method and apparatus for localization. First, it takes hours to accomplish these measurements and the neuronal source is assumed to be temporally and spatially constant. Second, the mathematical model used to attain source depth is valid only for a sphere, which the head is not. Third, the accuracy of localization is dependent on the signal-to-noise ratio, number of measurement points, and dipole orientation relative to the MEG measurement axis. Fourth, the algorithms used to fit theory to contour maps are computationally burdensome.

Moving the MEG from station to station causes three major problems. First, because of their extreme sensitivity and vector measurement capability, the prior art MEG devices can vibrate and give false signals due to their motion in the earth's static magnetic field. At each measurement station the experimental vibration spectrum is different. Second, present MEG devices are cryogenically cooled with liquid helium (i.e., they are superconducting magnetometers). Movement of these sensors from station to station around the head to generate contour maps causes inaccuracies in calibration due to tilt and changes in helium levels. Third, at each new station or measurement point the magnetic balance or magnetic nulling of device noise with internal magnetic trim tabs changes, giving rise to another calibration error.

Wynn et al, in an article entitled "Advanced superconducting gradiometer/magnetometer arrays and a novel signal processing technique", *IEEE Trans. Mag.*, Vol. 2, pg. 701, 1975, showed that a five-axis gradiometer magnetometer can provide a three-dimensional localization and track of a large source strength, static, ferrous magnetic dipole at ranges from tens of feet to thousands of feet, according to the dipole source strength and magnetometer sensitivity. Their device used magnetic sensors spaced many inches apart, not intended or designed for neuromagnetic measurements. They also showed that a simpler three-axis device could provide two-dimensional location and track of larger dipole objects. In summary, neuromagnetic localization with prior art MEG devices uses single point measurements that provide data to create a spatial magnetic contour map as the device is moved from station to station. These MEG measurements are inadequate for many reasons:

a. Because of their extreme sensitivity and vector measurement capability, the prior art MEG devices can vibrate and give false signals due to their motion in the earth's static magnetic field. At each measurement station the experimental vibration spectrum is different.

b. Prior art MEG devices are cryogenically cooled with liquid helium (e.g., they are superconducting magnetometers). Movement of these sensors from station to station around the head to generate contour maps causes inaccuracies in calibration due to tilt and changes in helium levels.

c. At each new station or measurement point the magnetic balance or magnetic nulling of device noise with internal magnetic trim tabs changes, giving rise to another calibration error.

d. It can take several hours to complete the data matrix of measurement positions and the neuronal source may not remain the same over that time period for valid localization.

e. The localization accuracy under this method is dependent on fitting measurement data to a mathematical model chosen to fit the magnetic contour and the spatial density of data measurement positions. This precludes real-time or near real-time determination of source location.
f. The localization accuracy is dependent upon the orientation of the generating neuronal source relative to the MEG sensor axis.
g. Localization algorithms used to fit theory to the contour map data matrix are computationally burdensome.

SUMMARY OF THE INVENTION

The present invention overcomes the aforementioned problems of the prior art magnetoencephalographic (MEG) devices. The present inventors realized that a multi-axis gradiometer could be used to locate and track neuronal magnetic fields from a single measurement station. The invention includes a system of three detection coils (each of the second, third, or fourth differencing single-axis gradiometer type) packaged in a small sensor situated beside the head so that each coil can independently sense the magnetic field from a physically small neuromagnetic dipole. All three magnetic sensors are oriented to measure the same Cartesian vector component (z) of the emanated neuromagnetic field ($H_z$), but at positions that are spaced laterally along the other two Cartesian directions (x and y). The signals from each single-axis gradiometer sensor are differenced with each other to give the lateral spatial gradients of the measured field ($\Delta H_z/\Delta x$, $\Delta H_z/\Delta y$). These spatial gradient-difference fields are then mathematically combined, either in electronic analog hardware or in a computer to give the lateral, 2-dimensional (x,y) location in the brain of the dipole generating the neuromagnetic field. A 3-dimensional location of the dipole can be established if two orthogonally placed sensors are used.

A first novel feature of the invention is its ability to measure and localize in two dimensions the generating dipole from a single measurement position.

A second novel feature of the invention is its ability to measure and localize the generating dipole almost instantaneously for large amplitude dipole sources and within minutes for small amplitude dipole sources.

A third novel feature of the invention is the use of three separate single-axis gradiometer-type magnetic sensors to reduce the effects of background noise interference.

A fourth novel feature of the invention is the ability for three-dimensional localization of the generating dipole from only two measurement positions with either one device moved once or two identical devices positioned orthogonally.

BRIEF DESCRIPTION OF THE DRAWINGS

In order that the present invention may be more fully understood it will now de described, by way of example, with reference to the accompanying drawings.

FIG. 2 is a diagram of single-axis magnetic detector coil configurations.

DESCRIPTION OF THE PREFERRED EMBODIMENTS

Figure 1:
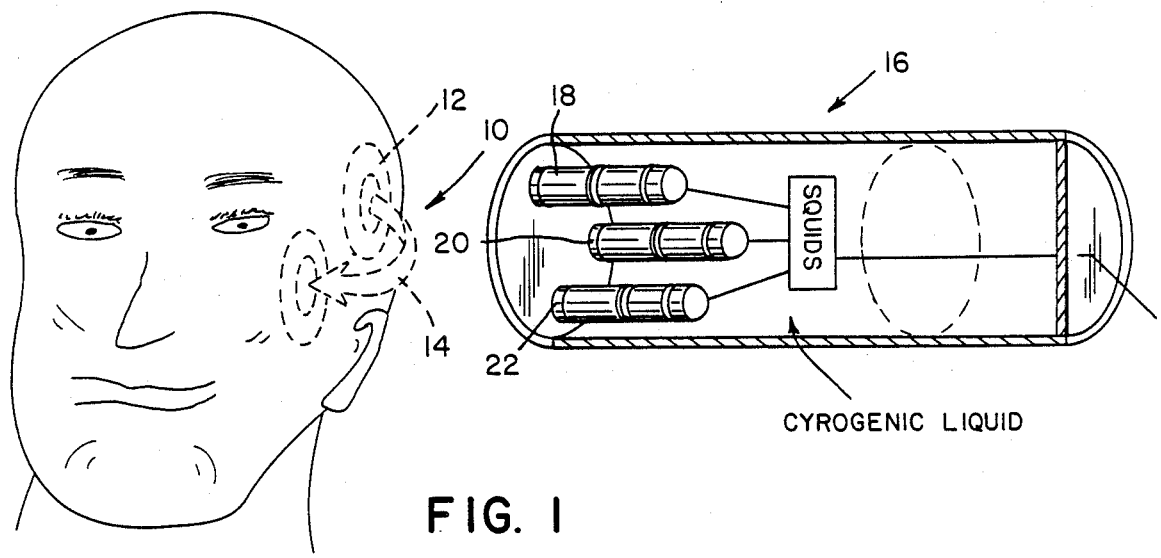
FIG. 1 is a block diagrammatic drawing of the invented MEG sensor as used to localize neuronal sources.

Neuromagnetic signals of physiological significance originate from sources in the brain that can be modeled by a current dipole. The current dipole generates a magnetic field 10 (see FIG. 1) which is the neuromagnetic field to be measured by the present invention. This neuromagnetic field has a field spatial pattern giving contours of constant field 12 (plus contours for B field vectors 14). The magnitude of the field diminishes as the contour radius increases.

The sensor portion of the invention 16 includes three single-axis type magnetometers (18, 20, 22), each of the second, third or fourth differencing single-axis gradiometer type. All three magnetic sensors are oriented to measure the same Cartesian vector component (z) of the emanated neuromagnetic field (Hz), but at positions that are spaced laterally along the other two Cartesian directions (x and y). The three single-axis magnetometers are generally positioned in a cryogenic liquid to attain the required sensitivity. Generally the superconducting coils of the magnetometers are connected to SQUIDS (superconductivity quantum interference devices) but any sensor can be used if it provides sensitivities from 5 to 500 femto Tesla. The signals from each single axis gradiometer sensor is differenced with each other to give the lateral spatial gradients of the measured field ($\Delta H_z/\Delta x$, $\Delta H_z/\Delta y$). These spatial gradient differenced fields are then mathematically combined, either in electronic analog hardware or in a computer to give the lateral, 2-dimensional (x,y) location in the brain of the dipole generating the neuromagnetic field. Taking the difference between sensors 18 and 20 gives the gradient:

$$\frac{H_1 - H_2}{\Delta x} = \frac{\Delta H_z}{\Delta x} = H_{zx}$$

Taking the difference between sensors 20 and 22 gives the gradient:

$$\frac{H_2 - H_3}{\Delta y} = \frac{\Delta H_z}{\Delta y} = H_{zy}$$

The x and y location of the dipole is given by:

$$X = \frac{-3H_z H_{zx}}{H_{zx}^2 + H_{zy}^2}$$

$$Y = \frac{-3H_z H_{zy}}{H_{zx}^2 + H_{zy}^2}$$

and the vertical magnetic movement source strength, Mz, of the neuromagnetic dipole is given by:

$$M_z = -H_z(x^2+y^2)^{\frac{1}{2}}$$

Figure 2A:
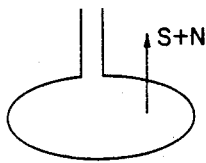
FIG. 2a is a single coil magnetometer.
Figure 2B:
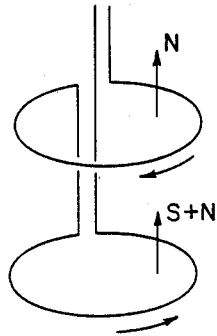
FIG. 2b is a first order gradiometer.
Figure 2C:
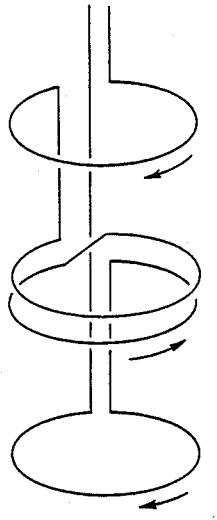
FIG. 2c is a second order gradiometer.
Figure 2D:
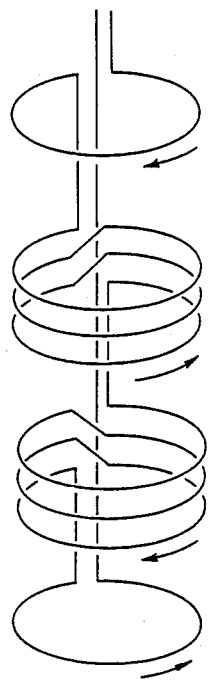
FIG. 2d is a third order gradiometer.

The choice of the type of coil used for each of the single-axis magnetometers (18, 20, 22) is dependent on the noise environment and whether magnetic shield enclosures are used. The specific magnetometers (18, 20, 22) shown in FIG. 1 are each superconducting second differencing gradiometers. FIG. 2 illustrates a variety of single-axis magnetometers that can be used with the present invention, although other types may be used as well. In FIG. 2a a single pickup coil detects the neuromagnetic signal, S, plus noise, N. The noise field, N, can be a factor of ten thousand times larger than the neuromagnetic signal, S. Generally, the noise originates from sources distant from the biological signal and the noise field is spatially uniform. Then, a second pickup coil, usually spaced several centimeters from the signal coil, is used to measure just the noise field, N, and not the neuromagnetic biologic signal. FIG. 2b shows this arrangement of two coils. When the output of each coil is subtracted from the other, this first order difference subtracts out the spatially uniform noise field and reveals the signal. This difference can be accomplished using one wire and winding the coils in opposing directions, as shown in FIG. 2b. Such a simple, one-difference device is called a single-differencing (or first order) gradiometer. If the noise field is not spatially uniform but varies linearly with distance, another two coils are used, as shown in FIG. 2c, to form a difference of a difference (i.e., double difference) to cancel the noise. Such a device is called a double-differencing (or second order) gradiometer. If the noise field varies quadratically with distance, then a third-differencing (or third order) gradiometer, FIG. 2d, is used.

These gradiometer magnetometers can have multi-turn coils that are immersed in a cryogenic fluid such as liquid helium to allow the coils to become superconducting. The superconducting loops can be connected to a SQUID (superconducting quantum interference device), which is usually another wire loop with a Josephson tunneling junction used to detect the current flowing in the pickup loop.

Figure 3:
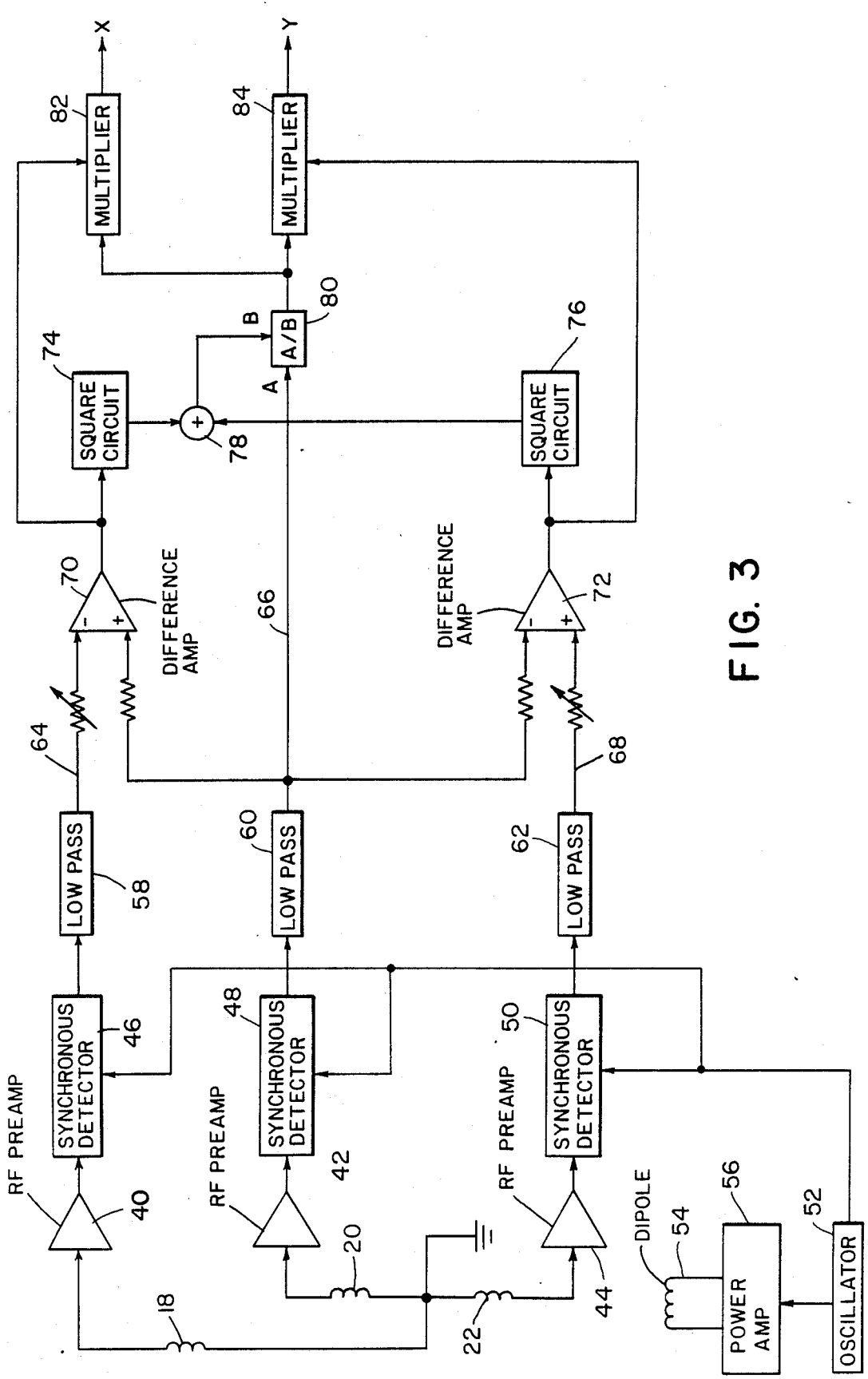
FIG. 3 is a schematic block diagram of an analog electronic circuit that can be used to mathematically provide two-dimensional localization.

FIG. 3 is a schematic drawing showing analog electronics that can be used to perform the above described calculations. Output from the three single-axis magnetometers 18, 20, 22 are input to the analog circuit and Cartesian coordinates (x, y) are generated indicating the two-dimensional location of the neuromagnetic dipole.

Output from the three magnetometers 18, 20, 22 are first input to RF preamplifiers 40, 42, 44 and each amplified signal is synchronously detected by synchronous detectors 46, 48, 50. Each synchronous detector is triggered by a synchronous sensor which may be an output current oscillator 52 driven through coil 54 and power amplifier 56 by the dipole source that is being detected and tracked. Other suitable means for providing a synchronous signal are also contemplated by the Applicants as outlined in the discussions concerning FIG. 4. The output from each synchronous detector passes through low pass filters 58, 60, 62 producing output signals 64, 66, 68 which represent the magnetic field strength $H_1$, $H_2$ and $H_3$, respectively. Signals $H_1$ (64) and $H_2$ (66) are differenced by difference amplifier 70 to give $$H_{zx} = \frac{H_1 - H_2}{\Delta x}$$

as an output. Similarly, signals $H_2$ (66) and $H_3$ (68) are differenced by difference amplifier 72 to give $$H_{zy} = \frac{H_2 - H_3}{\Delta y}$$

as an output. These difference amplifier outputs ($H_{zx}$ and $H_{zy}$) are each passed through squaring circuits 74, 76 to give $H^2_{zx}$ and $H^2_{zy}$, respectively. The squared signals $H^2_{zx}$ and $H^2_{zy}$ are then added by adder 78 to produce ($H^2_{zx} + H^2_{zy}$). The signal (66), which shall be called $H_z$, and the squared product ($H^2_{zx} + H^2_{zy}$) are input to a divided circuit 80. The output from the divide circuit 80 inputs to multiplier 82 and 84. Multiplier 84 multiplies the output from the divider 80

$$\frac{(H_z)}{H^2_{zx} + H^2_{zy}}$$

with the output from difference amplifier 70 ($H_{zx}$) to produce the x-axis output:

$$x = \frac{H_{zx} H_z}{H^2_{zx} + H^2_{zy}}.$$

Multiplier 84 multiplies the output from divide cicuirt 80

$$\frac{(H_z)}{H^2_{zx} + H^2_{zy}}$$

with output from difference amplifier 72 ($H_{zy}$) to produce the y-axis output:

$$y = \frac{H_{zy} H_z}{H^2_{zx} + H^2_{xy}}.$$

To make these outputs agree with the sign inversion and factor of 3 appearing in the previously disclosed equations for "x" of "y", the gain of the display device (not shown) is appropriately adjusted. The analogue circuit can be replaced by a computer to provide same two-dimensional location calculations.

For three dimensional localization, that is localization not only along a plane, but three dimensionally within the brain, two techniques are possible with the present invention. First, after taking the measurement with sensor 16 located in one plane (see FIG. 1) it can be moved to a second measurement position orthogonal to the first measured position. These two readings will provide three-dimensional localization. Secondly, two sensors 16 can be used and orthogonally oriented (i.e., one can be positioned at the side of the head and the other can be looking down from the top of the head). This second technique would allow the neuromagnetic event to be observed simultaneously in both planes.

Figure 4:
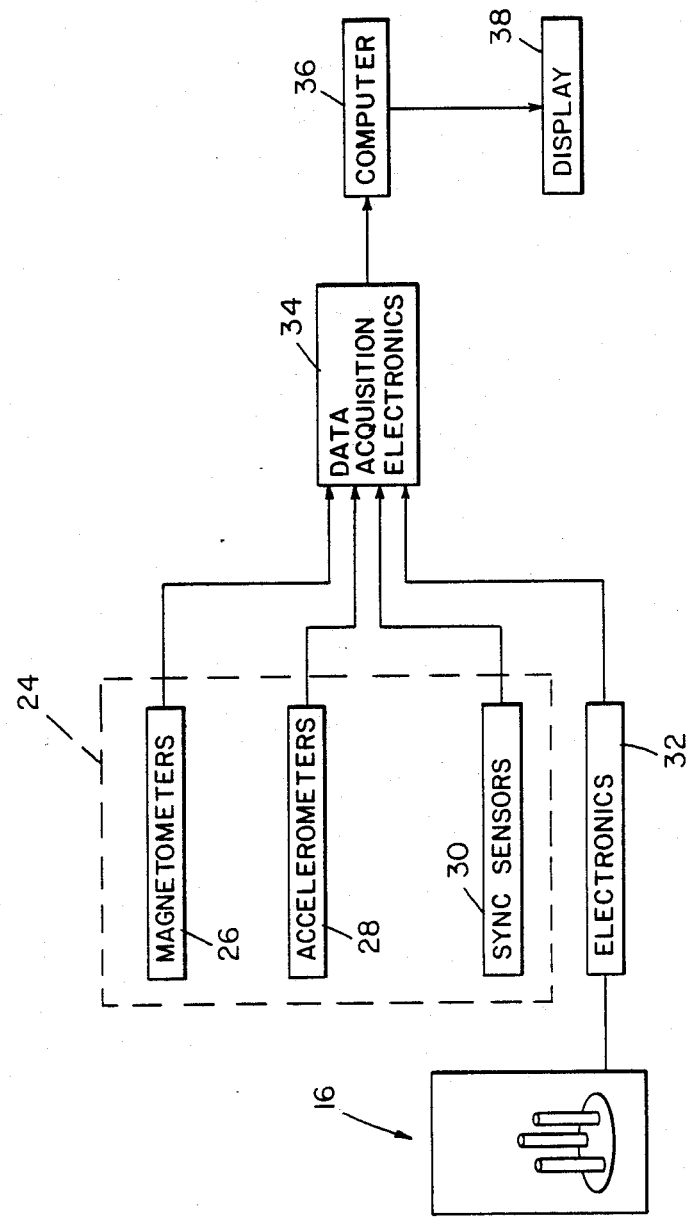
FIG. 4 is a system block diagram of a complete neuromagnetic localization system as taught by the present invention.

FIG. 4 gives an example of a system diagram of the present invention with auxiliary sensors 24 to help reduce noise contamination due to sensor vibration, external transitory magnetic anomalies, and unwanted biomagnetic signals from the subject. The auxiliary sensors can include magnetometers 26, accelerometers 28 (to detect sensor motion or vibration), and a sync sensor 30 (for example, one or two EEG channels to help initialize or trigger the localization process). Input from the auxiliary sensors 24 and the data acquisition electronics 32 are input to an adaptive signal processing means that would include data acquisition electronics 34 and a computer 36 for processing an adaptive filtering algorithm. The location of the neuromagnetic dipole is then indicated on display 38.

It will be understood that various changes in the details, materials, arrangement of parts and operational conditions which have been herein described and illustrated in order to explain the nature of the invention may be made by those skilled in the art within the principles and scope of the present invention. Whereas the description of the preferred embodiment has been described in the context of detecting neuromagnetic signals emanating from the brain, it is to be understood that the present invention can detect neuromagnetic signals emanating from other sites of the neurological system.

Having set forth the nature of the invention, what is claimed is:

1. A method for locating sources of magnetic signals emanating from a patient, comprising the steps of:
    positioning a first bundle of at least three single-axis magnetometers near a patient with the magnetometers oriented to measure the same vector component (z) of the biomagnetic field but with the magnetometers laterally displaced from each other;
    differencing signals obtained from sets of two magnetometers to calculate lateral spatial gradients of the measured biomagnetic field; and,
    calculating a two-dimensional location for the source of the biomagnetic field by analyzing the lateral spatial gradients.

2. The method of claim 1, wherein said differencing step is performed using differential amplifiers.

3. The method of claim 1, wherein said step of differencing further comprises using a computer to perform the steps of:
    taking the difference between signals ($H_1$, $H_2$) measured in two adjacent magnetometers displaced by x to calculate the lateral spatial gradient $H_{zx}$:

$$\frac{H_1 - H_2}{\Delta x} = \frac{\Delta H_z}{\Delta x} = H_{zx}; \text{ and,}$$

taking the difference between signals ($H_2$, $H_3$) measured in two adjacent magnetometers displaced by y to calculate the lateral spatial gradient $H_{zy}$:

$$\frac{H_2 - H_3}{\Delta y} = \frac{\Delta H_z}{\Delta y} = H_{zy}.$$

4. The method of claim 3, wherein said step of calculating the two-dimensional location is performed by using squaring circuits, an add circuit, a divide circuit and two multiplier circuits to perform the following data manipulations:

$$x = \frac{-3 H_z H_{zx}}{H_{zx}^2 + H_{zy}^2}$$

$$y = \frac{-3 H_z H_{zy}}{H_{zx}^2 + H_{zy}^2}$$

5. The method of claim 3, wherein said step of calculating the two-dimensional location further comprises the step of using a computer to calculate the x and y location of the source of a biomagnetic signal using the lateral spatial gradients ($H_{zx}$, $H_{zy}$) as follows:

$$x = \frac{-3 H_z H_{zx}}{H_{zx}^2 + H_{zy}^2}$$

$$y = \frac{-3 H_z H_{zy}}{H_{zx}^2 + H_{zy}^2}$$

6. The method of claim 5, further comprising the step of: calculating the vertical magnetic-moment source strength ($M_z$) of the biomagnetic source using a computer, as follows:

$$M_z = -H_z (x^2 + y^2)^{\frac{3}{2}}.$$

7. The method of claim 1, further comprising the steps of:
    positioning a second bundle of at least three single axis magnetometers near a patient and oriented orthogonally from said first bundle of magnetometers, wherein the magnetometers in said second bundle are each oriented to measure the same vector component of the biomagnetic field but with the magnetometers laterally displaced from each other;
    differencing the signal from sets of two magnetometers located in said second bundle of magnetometers; and,
    calculating a three-dimensional location for the source of the biomagnetic field by analyzing the lateral spatial gradient determined by the first and second bundles of magnetometers.

* * * * *